United States Patent [19]
House

[11] Patent Number: 5,965,265
[45] Date of Patent: Oct. 12, 1999

[54] FUNCTIONALIZED SILICAS AS CORE SUPPORTS FOR CHIRAL STATIONARY PHASES

[75] Inventor: David W. House, Arlington Heights, Ill.

[73] Assignee: UOP LLC, Des Plaines, Ill.

[21] Appl. No.: 08/978,413

[22] Filed: Nov. 25, 1997

[51] Int. Cl.⁶ ............. B01D 15/08; B01J 13/00; B32B 19/00
[52] U.S. Cl. ............. 428/405; 502/405; 516/101; 530/417
[58] Field of Search ............. 252/315.2; 428/405; 502/405; 516/101; 530/417

[56] References Cited

U.S. PATENT DOCUMENTS

| | | | |
|---|---|---|---|
| 4,377,482 | 3/1983 | Rivier | 530/417 X |
| 4,469,630 | 9/1984 | Flashner | 530/417 X |
| 4,530,894 | 7/1985 | Imamura et al. | 428/405 X |
| 4,755,294 | 7/1988 | Pradet et al. | 252/315.2 X |
| 4,767,670 | 8/1988 | Cox et al. | 428/405 X |
| 4,902,570 | 2/1990 | Heinemann et al. | 428/405 |
| 5,695,882 | 12/1997 | Rosenberg | 428/405 |

*Primary Examiner*—Richard D. Lovering
*Attorney, Agent, or Firm*—Thomas K. McBride; Frank S. Molinaro; Maryann Maas

[57] ABSTRACT

Functionalized silicas which can be used as core supports for a broad variety of chiral stationary phases may be conceptually represented as T—O—Si—U. T represents a refractory inorganic oxide, and T—O—Si arises from reaction of an organosilane with the surface hydroxyl groups of the refractory inorganic oxide. U represents a polyamine, related to poly(ethyleneamines), tris(2-aminoethyl) amine, or alkyleneoxyamines of glycerine.

5 Claims, No Drawings

FUNCTIONALIZED SILICAS AS CORE SUPPORTS FOR CHIRAL STATIONARY PHASES

BACKGROUND OF THE INVENTION

Ever since Pasteur discovered the property of optical activity displayed by chiral compounds, the resolution of racemic mixtures into their enantiomeric components has posed a challenge. Substantial progress in separating enantiomeric pairs has been achieved since Pasteur's laborious hand separation of the enantiomeric crystals of racemic sodium ammonium tartrate, yet methods of resolution, and the materials used therefor, remain a formidable obstacle to commercial production of optically active organic substances.

A traditional method of resolution comprises reacting a racemic mixture with a second optically active substance to form a pair of diastereomeric derivatives. Such derivatives generally have different physical properties which permit their separation by conventional means. For example, fractional crystallization often permits substantial separation to afford at least one of the diastereomers in a pure state, or largely so. An appropriate chemical transformation then converts the purified derivative, which was formed initially solely to prepare a diastereomeric pair, into one enantiomer of the originally racemic compound. This traditional method is exemplified by the reaction of naturally occurring optically active alkaloids, for example brucine, with racemic acids to form diastereomeric salts, with release of an optically active organic acid from a purified diastereomer upon acidification of the latter.

Such traditional methods suffer from many limitations. Generally, only one of the enantiomeric pairs can be obtained, so yields are necessarily less than 50%. The separation of the material so obtained usually is incomplete, leading to materials with enhanced rather than complete optical purity. The optically active materials used to form the diastereomers frequently are expensive and quite toxic—the alkaloids as a class are good examples—and are only partially recoverable. Regeneration of optically active material from its derivative may itself cause racemization of the desired compound, leading to diminution of optical purity. For example if optically active benzyl alcohols are prepared through their diastereomeric ester derivatives, subsequent acid hydrolysis of the latter to regenerate the alcohol may be accompanied by appreciable racemization.

With the advent of chromatography diverse variations on the basic theme of separating diastereomers became possible. These approaches undeniably represent substantial advances in the art, yet fail to surmount the basic need, and associated problems, to prepare diastereomeric derivatives of the desired compound and to transform such derivatives after separation to the optically active compounds of interest.

Chromatographic methods of separating diastereomers offer the advantages of general application, mild conditions which generally preclude chemical or physical transformation, efficiency of recovery and separation which are limited only by the number of theoretical plates employed, and the capability of utilization from a milligram to kilogram scale. Translation from a laboratory to industrial scale has proved feasible, and commercial processes employing chromatographic separation occupy an important position in the arsenal of available industrial methods. For such reasons, methods based on chromatographic separation remain under intensive exploration.

To circumvent the disadvantage of separating diastereomeric derivatives of a compound while retaining the advantage of chromatographic separation, recent advances in the art have employed chiral, optically active compounds in association with the chromatographic support. The theory underlying this approach is that chiral material will have weak interactions with enantiomers, for example, hydrogen bonding, or acid-base interactions generally. Such weak interactions lead to reversible formation of (diastereomeric) entities which we refer to as complexes, and the equilibrium constant characterizing complex formation will be different for each member of the enantiomeric pair. The different equilibrium constants manifest themselves as a differing partition coefficient among the phases in a chromatographic process, leading ultimately to separation of enantiomers.

Thus, enantiomers of some chromium complexes were resolved by chromatography on powdered quartz, a naturally occurring chiral material. Karagounis and Coumolos, *Nature*, 142, 162 (1938). Lactose, another naturally occurring chiral material, was used to separate p-phenylene-bis-iminocamphor. Henderson and Rule, *Nature*, 141, 917 (1938). However, despite this knowledge substantiating theoretical considerations, advances in the art have been tortuous at best.

A major obstacle has been the development of a chiral solid phase with the capability of resolving a broad class of racemic organic compounds, with a stability which permits repeated usage, and with adequate capacity to make separation feasible on a preparative scale. Gil-Av has made a major contribution toward one kind of solution by gas-liquid phase chromatographic resolution of enantiomers using columns coated with N-trifluoroacetyl derivatives of amino acids, di-and tri-peptides. Gil-Av and Nurok, "Advances in Chromatography", Vol. 10, Marcel Dekker (New York), 1974. However, the advances suffer practical limitations originating from the need to have volatile substrates and the inability to scale up the methods employed.

Another advance is represented by the work of Baczuk and coworkers, *J. Chromatogr.*, 60, 351 (1971), who covalently bonded an optically active amino acid through a cyanuric acid linkage to a modified dextran support and utilized the resulting material in column chromatography to resolve 3,4-dihydroxyphenylalanine. A different approach is exemplified by polymerization of optically active amides with the resulting polymer used as a solid phase in liquid-solid chromatography. Blaschke and Schwanghart, *Chemische Berichte*, 109, 1967 (1976).

More recently it has become an accepted reality that enantiomeric medicinals may have radically different pharmacological activity. For example, the (R)-isomer of propranolol is a contraceptive whereas the (S)-isomer is a beta-blocker. An even more dramatic and tragic difference is furnished by thalidomide where the (R)-enantiomer is a safe and effective sedative when prescribed for the control of morning sickness during pregnancy whereas the (S)-enantiomer was discovered to be a potent teratogen leaving in its wake a multitude of infants deformed at birth. This has, in part, provided the motivation for developing additional tools for chiral separations. Chromatographic processes, especially liquid chromatography, appear to offer the best prospects for chiral separations. One variant of the latter utilizes achiral eluents in combination with chiral stationary phases (CSPs), which has the critical aspect that a variety of chiral stationary phases be available to the practitioner. In recent years substantial progress has been made by developing a class of chiral stationary phases based upon derivatized polysaccharides, especially cellulose, adsorbed on a carrier such as silica gel or a modified silica gel. This recently has been summarized by Y. Okamoto, *J. Chromatog.*, 666 (1994), 403–19.

It appeared to us that continued progress in chromatographic resolution of racemic mixtures depended upon developing chiral stationary phases which were more effective than the prior art ones in resolving racemic mixtures independent of chemical structure of the enantiomers, which were easily prepared from readily available materials, and which had as the underlying solid carrier (which we refer to herein as the core support) a structure which could either adsorb or covalently bond to chiral organic materials serving to mediate resolution. The latter properties of a core support would make available a progenitor to a chiral stationary phase (CSP) which could be utilized cheaply, effectively, and for a wide variety of CSPs. Thus, what we seek is material whose universality as a core support would be analogous to the hypothetical (and nonexistent) "universal solvent".

Our solution to the underlying problem of a universal core support is a series of functionalized refractory inorganic oxides bearing a multiplicity of amino groups covalently bonded to the underlying inorganic oxide. Silica is preferred as the inorganic oxide since it is well accepted as a chromatographic support, and indeed its properties make it somewhat unique as a support in chromatographic processes. Amino groups are used as a functional group since they serve as a mild Lewis base and afford strong dipolar interaction with many different kinds of organic materials so as to form quite stable CSPs where the chiral organic material is merely adsorbed on the underlying core support. Amino groups also can be used per se as a functional group for covalent attachment to chiral organic materials, or they can be readily modified to afford other reactive functional groups for subsequent covalent bonding to chiral organic materials. The result is a core support capable of much variation to prepare an enormous variety of CSPs, based on the chiral organic material which may be adsorbed on, or may be covalently bonded to, the core support.

SUMMARY OF THE INVENTION

The purpose of our invention is to provide core supports which may be used to prepare a broad variety of chiral stationary phases where the chiral organic material may be either adsorbed or covalently bonded to the core support. An embodiment comprises a refractory inorganic oxide with a surface area of at least 35 square meters per gram and having bound surface hydroxyl groups which are covalently bonded to a polyaminosilane via Si—O linkages. In one embodiment the polyamines are polyethylenaminosilanes. In another embodiment the polyamine is a polyaminoethoxylated glycerol.

DESCRIPTION OF THE INVENTION

The need for broadly-effective, "general-purpose" chiral stationary phases reflects the need for an underlying core support which may be employed in conjunction with a wide variety of chiral organic materials to provide chiral stationary phases based either on adsorption of the organic material by the core support, or covalent bonding of the organic material to the core support. We describe within core supports which provide the requisite flexibility, or universality, while remaining relatively inexpensive, and which are prepared rather simply, and thus are widely available. The core supports which are our invention are functionalized refractory inorganic oxides, especially silicas, where the silica has been modified via covalent attachment of a polyfunctional amine to the surface hydroxyl groups of the silica by silylation. Although the techniques employed are well known—which contribute to the universality of the core support—the core supports themselves have not previously been recognized, hence their broad applicability can not have been previously appreciated.

The core supports of our invention consist of a carrier, which is a refractory inorganic oxide, and a coating on the carrier which serves either as a layer which readily adsorbs many chiral organic materials, or which can serve to covalently bond to chiral organic materials via commonly found functional groups.

The carriers of our invention are refractory inorganic oxides which generally have a surface area of at least about 35 $m^2/g$, preferably greater than about 50 $m^2/g$ and more desirably greater than 100 $m^2/g$. There appears to be some advantage to working with materials having as high a surface area as possible, although many exceptions are known which preclude making this a general statement. It is required that the refractory inorganic oxide have bound surface hydroxyl groups, by which is meant not adsorbed water but rather hydroxyl (OH) groups whose oxygen is bound to the metal of the inorganic oxide. These latter hydroxyl groups sometimes have been referred to as chemically combined hydroxyl. Adsorbed water generally can be removed by calcination at temperatures which depend on the nature of the inorganic oxide, but which for alumina, as an example, are in the range 350–700° C. Suitable refractory inorganic oxides include alumina, titania, zirconia, chromia, silica, boria, silica-alumina and combinations thereof. Of these, silica is particularly preferred as a carrier in chromatographic separations.

The core supports of our invention may be represented, at least graphically, by the structure

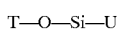

T represents the refractory inorganic oxide whose nature has already been discussed. Such refractory inorganic oxides have previously been stated to have bound surface hydroxyl groups which can be represented as T—OH; the partial structure T—O of our core support arises from the bound surface hydroxyl groups which react with a silane to form the O—Si covalent linkage. The exact origin of this linkage will be discussed within.

U is a polyamine which is selected from the polyamines I, II and III as represented below:

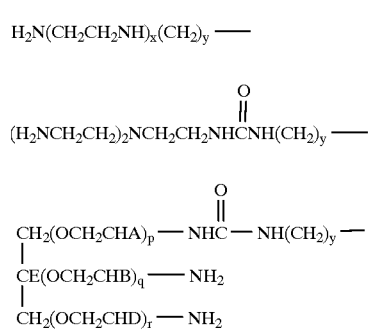

In the aforegoing structures, x is an integer from 1 up to about 10, but most preferably is 2, 3, or 4. The value y also is an integer from 2 to 4, and most usually is 3. The groups A, B, D and E are each selected from the groups consisting of hydrogen and lower alkyl containing from one up through 4 carbon atoms. The subscripts p, q and r also are integers from 1 up through about 10. It is readily seen that I is related to poly(ethylene amines), the structure II is related to tris(2-aminoethyl)amine and the structure III is related to alkyleneoxyamines of glycerine.

Returning to the structure of our core support, T—O—Si—U, the origin of the O—Si bond can now be more readily appreciated. For example, in those cases where U corresponds to structure I, the core support results from the reaction of the bound surface hydroxyl groups of the refractory inorganic oxide with materials of formula

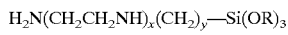

$H_2N(CH_2CH_2NH)_x(CH_2)_y—Si(OR)_3$

Thus, U has a trialkoxysilane functionality attached at one terminus. Generally these alkoxy groups are either methoxy or ethoxy groups, but their nature is not important to the success of our invention. It is the terminal silane functionality which reacts with the bound hydroxyl groups of the refractory inorganic oxide to afford the Si—O bond present in the core supports of our invention. The core supports where U is represented by II or III are formed somewhat differently in that an isocyanatosilane is reacted with the bound surface hydroxyl groups of the refractory inorganic oxide with formation of silicon-oxygen covalent linkages. The isocyanato group, OCN, then is reacted with the hydrogens of primary or secondary amines to afford the urea linkages found in II and III.

Our invention is more easily understood with the help of the following examples. However, it needs to be clearly understood that our invention is not limited thereby, but that the examples merely illustrate our invention.

EXAMPLES

General Synthesis of Polyaminoorganosilane-Modified Silica Gel

To a 100 mL, three-necked, round-bottomed flask equipped with a Dean-Stark trap, a reflux condenser attached to the trap, a thermometer (attached to a Therm-o-watch temperature controller), a Teflon-coated stirring bar, a heating mantle, and a nitrogen line attached to the top of the condenser were added 7.00 g of 5 u silica gel (Adsorbosphere from Alltech Associates) and 50 mL of dry toluene. The reaction was heated to reflux under a nitrogen atmosphere and the slurry was gently stirred. After any water had been azeotropically removed and the trap cleaned, about 6 to 7 mmol of the polyaminoorganotrialkoxysilane (whose preparation is described below) were added. Refluxing was continued to remove ethanol (in the case of the trialkoxy being triethoxy) in order to drive the reaction between the polyaminoorganotrialkoxysilane and the silica gel to the right. The first several volumes of distillate in the Dean-Stark trap were discarded and fresh toluene was added in an amount equal to that discarded. The reaction was allowed to proceed for 24 hours, during which, the trap was periodically emptied and fresh, dry toluene was added to the reaction. Analysis of the reaction liquid by FT-IR (Fourier transform infrared spectroscopy) was used to insure that enough polyaminoorganotrialkoxysilane was employed.

After 24 hours, the reaction was stopped, allowed to cool, and the white slurry isolated by filtration using a sintered glass funnel and a Buchner flask. The filter cake was washed sequentially with (3×25 mL) of dry toluene, methanol, acetone, and finally pentane to yield the modified silica gel powder. The modified silica gel was transferred to a glass bottle and placed in a vacuum oven at 100° C. for 2 hours to yield solvent-free material.

Synthesis of Tris-(2-aminoethyl)-amine-modified 3-Isocyanato-propyltriethoxysilane (TAEA)

To 1.13 g (7.437 mmol, 96%) of tris-(2-aminoethyl)-amine (Aldrich Chemical Co.) in a 100 mL, three-necked, round-bottomed flask equipped with a reflux condenser, Teflon-coated stirring bar, equilibrated dropping funnel (attached to the reflux condenser), magnetic stirrer, and a heating mantle (attached to a Therm-o-watch temperature controller) were added 40 mL of toluene. The reaction vessel was kept under a nitrogen atmosphere. To the dropping funnel were added 1.61 g (6.198 mmol, 95%) of isocyanato-propyltriethoxysilane (United Chemical Technologies, Inc.) dissolved in 10 mL of dry toluene which, in turn, were added dropwise (1 drop/5 seconds) to the reaction solution at room temperature. A three degree exotherm was observed. The progress of the reaction was monitored by following the disappearance of the isocyanate band in the FT-IR. After addition of 1.00 equivalents of the isocyanatopropyltriethoxysilane (based on 1.20 equivalent of the polyamine) and verification that no more unreacted isocyanate was present, the polyfunctionalized organosilane was ready for attachment to the silica gel and utilized per se.

Synthesis of a Polyoxypropylenetriamine-modified 3-Isocyanato-propyltriethoxysilane To 3.22 g (7.289 mmol) of a polyoxypropylenetriamine based on structure III (sold under the name of Jeffamine T-403 from Huntsman Chemical Co.), where $E=C_2H_5$ and p+q+r~5.3, in a 100 mL, three-necked, round-bottomed flask equipped with a reflux condenser, Teflon-coated stirring bar, equilibrated dropping funnel (attached to the reflux condenser), magnetic stirrer, and a heating mantle (attached to a Therm-o-watch temperature controller) were added 40 mL of dry toluene. The reaction vessel was kept under a nitrogen atmosphere. A solution of 1.582 g (6.074 mmol, 95%) of isocyanatopropyltriethoxysilane in 10 mL of dry toluene was added dropwise (1 drop/5 seconds) to the reaction solution at room temperature. A three degree exotherm was observed. The progress of the reaction was monitored by following the disappearance of the isocyanate band in the FT-IR. After addition of 1.00 equivalents of the isocyanatopropyltriethoxysilane (based on 1.20 equivalent of the polyamine) and verification that no more unreacted isocyanate was present, the polyfunctionalized organosilane was ready for attachment to the silica gel and utilized per se.

Trimethoxysilylpropyldiethylenetriamine (DETA)

Trimethoxysilyl-propyldiethylenetriamine (95% purity, FW=265.43) was obtained from United Chemical Technologies, Inc. and was used without further purification. The polyfunctionalized organosilane was attached to the silica gel using the method described above.

Ionic Coating of (R)-(−)-N-(3,5-Dinitrobenzoyl)-α-phenylglycine onto an Aminoorganosilane-modified Silica Gel Column To an aminoorganosilyl-modified silica gel column attached to a high performance liquid chromatograph were pumped 40 mL of a 50:50 mix of hexane and THF at a flow rate of 1.0 mL/min. The column was then treated with 30 mL of pure THF (flow rate of 2.0 mL/min). While maintaining the flow rate at 2.0 mL/min, about 50 mL of a 5% solution of anhydrous triethylamine in dry THF (2.50 g of triethylamine in 47.50 g of THF) were pumped through to ensure that the amino groups of the aminoorganosilyl-modified silica gel column were present as the free base. After completion of the base treatment, the column was washed with 50 mL of dry THF which was followed with a solution composed of 2.00 g of (R)-(−)-N-(3,5-dinitrobenzoyl)-α-phenylglycine dissolved in 50 mL of dry THF. After another wash with 40 mL of dry THF, the column was washed with 10% 2-propanol in hexane until the base line was constant. All washings were carried out using a liquid chromatography pump set at a flow rate of 2.0 mL/min.

I claim as my invention:

1. A chiral stationary phase represented by T—O—Si—U, where T is a refractory inorganic oxide with a surface of at least 35 m² per gram and having bound surface hydroxyl groups, O—Si is a covalent bond between said bound surface hydroxyl groups and the silicon atom of a silane, and U is a polyamine selected from the group consisting of polyamines with the formula

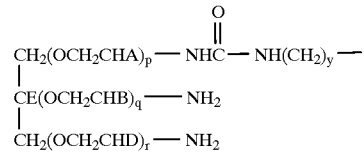

and

where x is an integer from 1 up to about 10, y is an integer from 2 to 4, A, B, D and E are selected from the group consisting of hydrogen and lower alkyl containing from 1 up through 4 carbon atoms, and p, q, and r are integers from 1 up through about 10, said polyamine further comprising an adsorbed or covalently bonded chiral organic material.

2. The chiral stationary phase of claim 1 where said refractory inorganic oxide is selected from the group consisting of alumina, titania, zirconia, chromia, silica, boria, silica-alumina, and combinations thereof.

3. The chiral stationary phase of claim 2 where the refractory inorganic oxide is silica.

4. The chiral stationary phase of claim 1 where said surface area is at least about 50 m² per gram.

5. The chiral stationary phase of claim 1 where said surface area is at least about 100 m² per gram.

* * * * *